United States Patent [19]

Maeda et al.

[11] Patent Number: 5,038,048
[45] Date of Patent: Aug. 6, 1991

[54] DEFECT DETECTION SYSTEM AND METHOD FOR PATTERN TO BE INSPACTED UTILIZING MULTIPLE-FOCUS IMAGE SIGNALS

[75] Inventors: Shunji Maeda; Htoshi Kubota, both of Kanagawa, Japan

[73] Assignee: Hitachi, Ltd., Tokyo, Japan

[21] Appl. No.: 454,356

[22] Filed: Dec. 21, 1989

[30] Foreign Application Priority Data

Dec. 23, 1988 [JP] Japan .................................. 63-323276

[51] Int. Cl.$^5$ ............................................. G01N 21/88
[52] U.S. Cl. ..................................... 250/563; 250/572
[58] Field of Search ............... 250/562, 563, 572, 548; 356/430–431; 358/106

[56] References Cited

U.S. PATENT DOCUMENTS

| | | | |
|---|---|---|---|
| 4,330,712 | 5/1982 | Yoshida | 250/572 |
| 4,513,441 | 4/1985 | Hemshaw | 250/562 |
| 4,685,139 | 8/1987 | Masuda et al. | 250/562 |
| 4,689,491 | 8/1987 | Lindow et al. | 250/572 |
| 4,707,610 | 11/1987 | Lindow et al. | 250/563 |

*Primary Examiner*—David C. Nelms
*Assistant Examiner*—Khaled Shami
*Attorney, Agent, or Firm*—Antonelli, Terry, Stout & Kraus

[57] ABSTRACT

A defect detection system and method for a pattern to be inspected wherein multiple-focus images of the pattern to be inspected are obtained and a defect on the pattern to be inspected is detected utilizing the multiple-focus images.

28 Claims, 18 Drawing Sheets

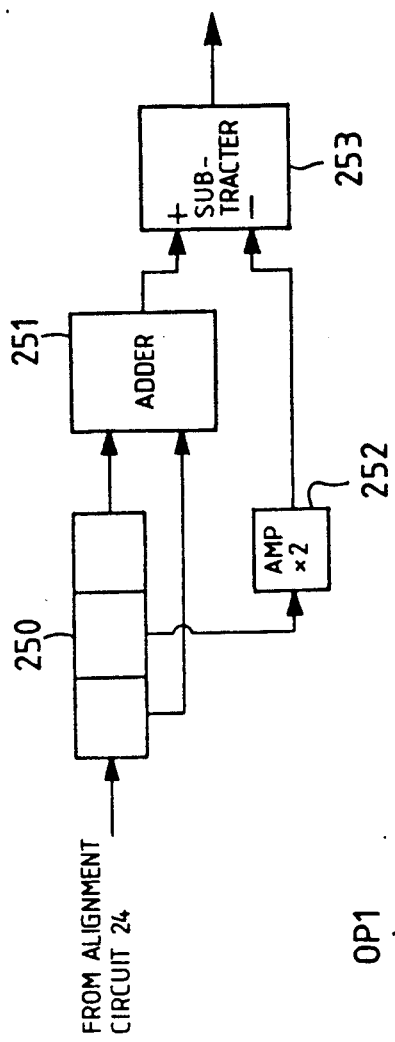
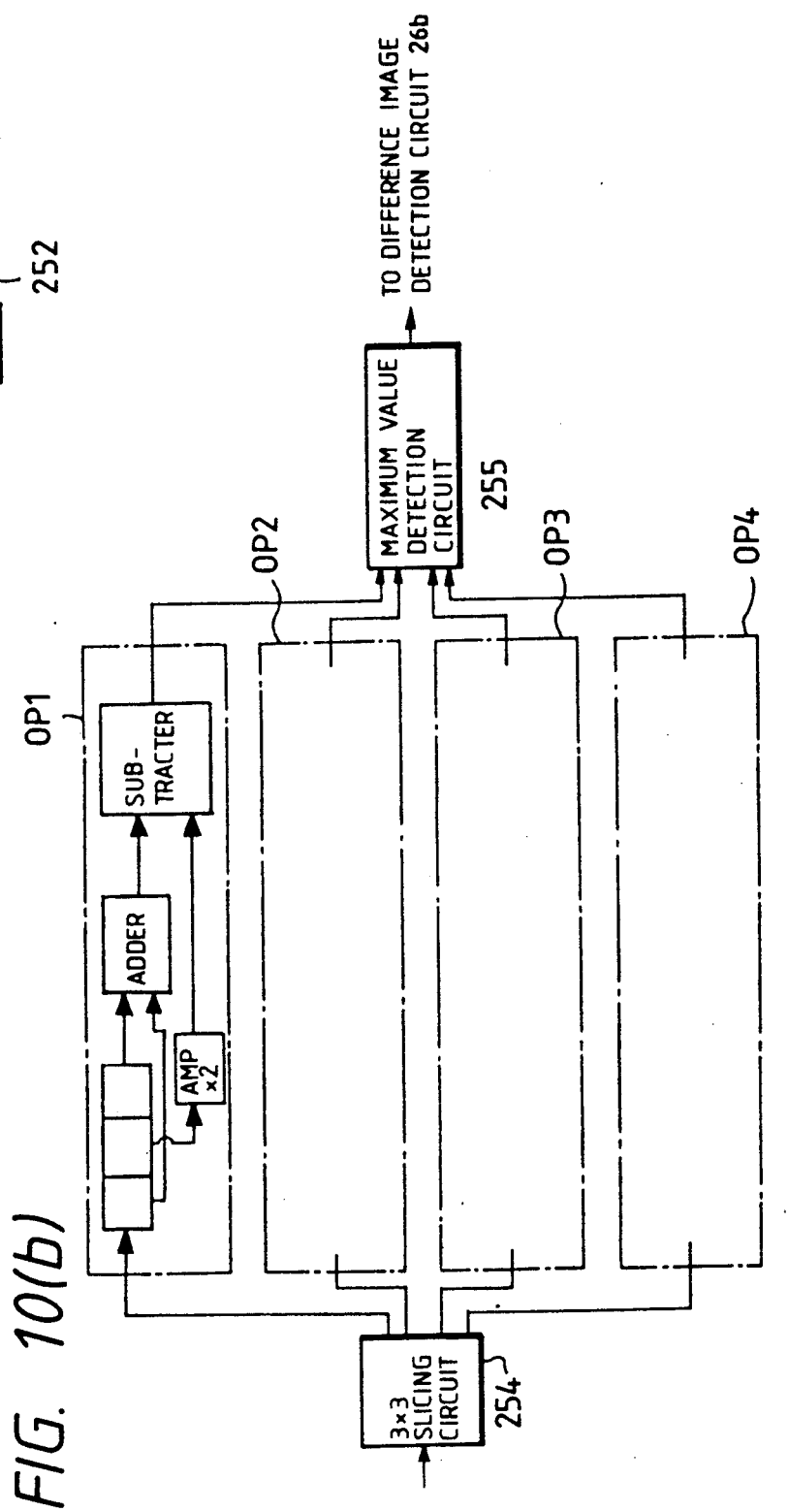

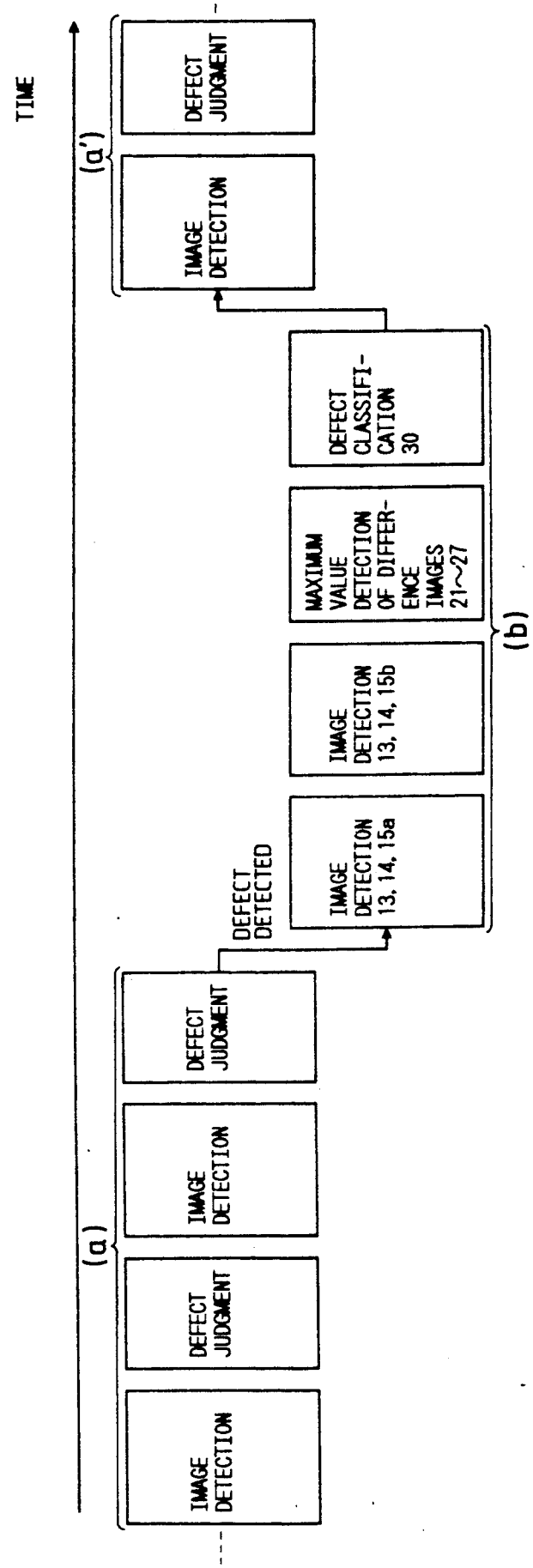

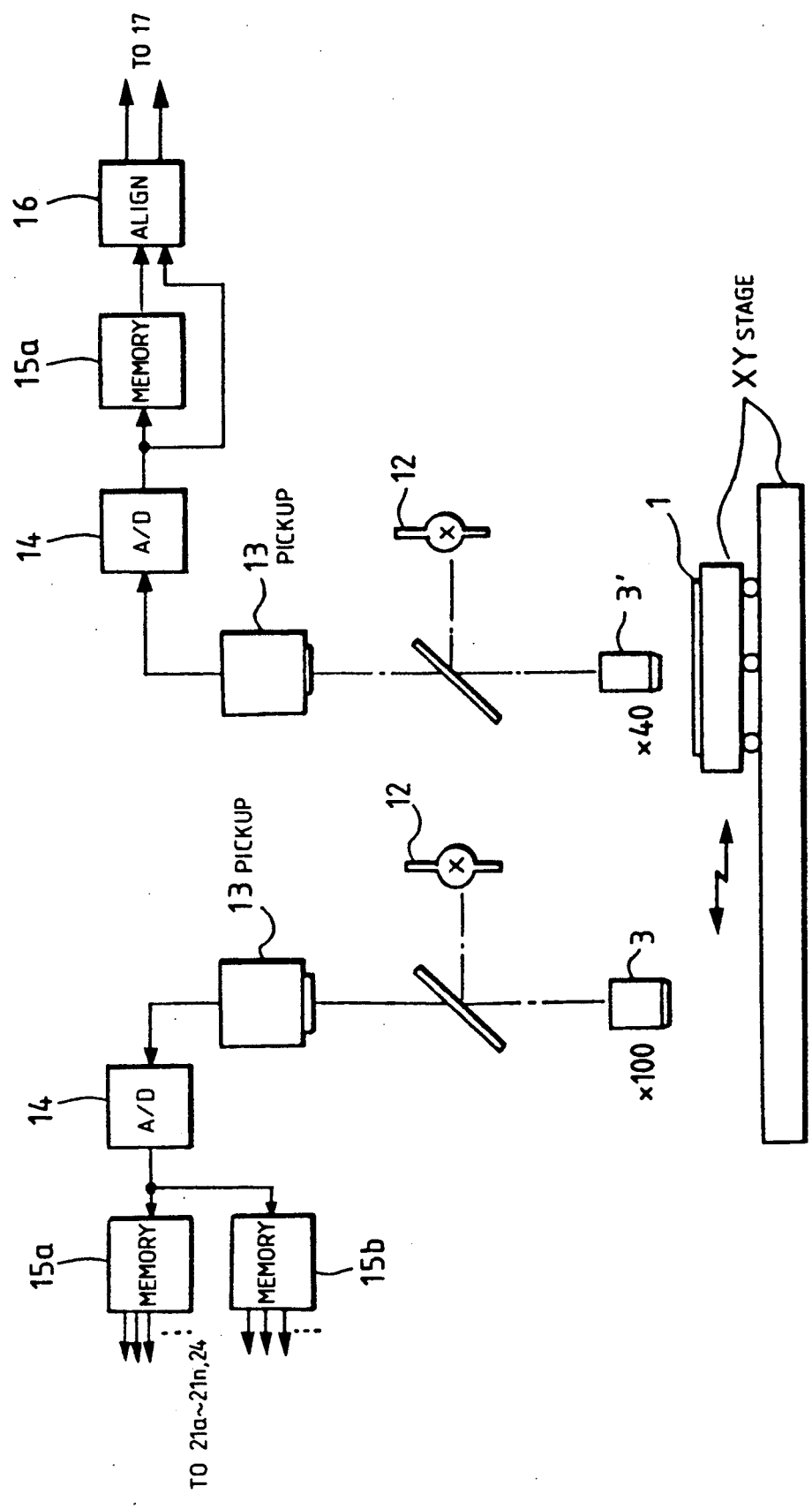

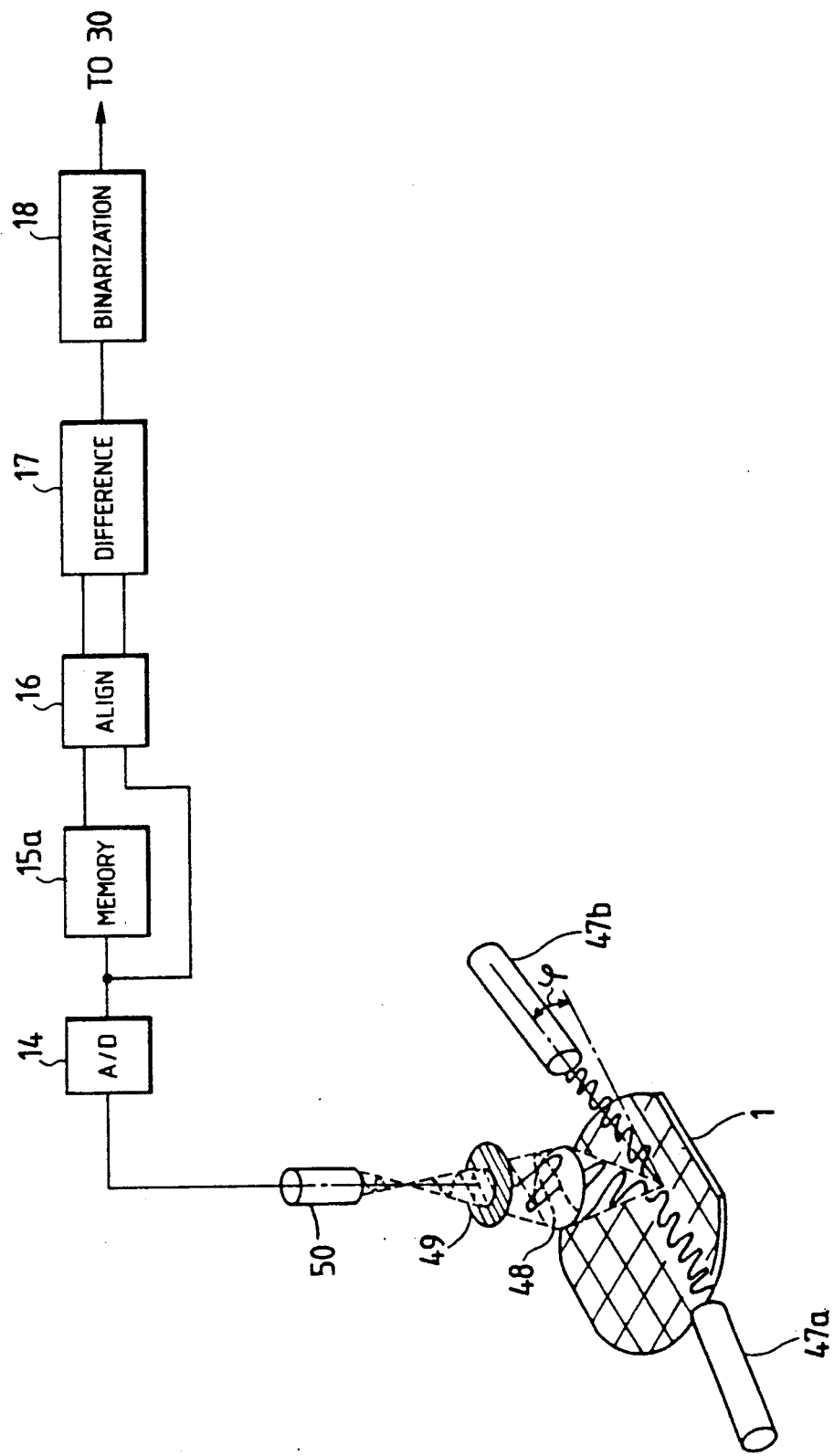

DEFECT DETECTION SYSTEM AND METHOD FOR PATTERN TO BE INSPECTED UTILIZING MULTIPLE-FOCUS IMAGE SIGNALS IMAGE

BACKGROUND OF THE INVENTION

The present invention relates to a defect detection method and the device for detecting a defect such as a foreign matter defect in the form of a contaminant, a discoloration defect, a deformation or pattern defect, etc. for LSI wafer patterns, etc.

Among conventional visual inspection systems, for example, the one described in Technical Journal, Vol. 87, No. 132 (1987), pp. 31 to 38, The Institute of Electronics and Communication Engineers of Japan is well known. Such a system is shown in FIG. 23 where a circuit pattern on a wafer 1 lighted with a lamp 2 is enlarged and detected with an image sensor 4 through an object lens 3, whereby a variable density image such as a gray scale image of the circuit pattern is obtained. The detected variable density image is compared with the image of the preceding chip 7a (adjacent chip) stored in an image memory 5 in a defect judgment circuit 6 for performing defect judgment. The detected image is simultaneously stored in the image memory 5 to be used for comparison with the next chip 7b.

An example of defect judgment is shown in FIG. 24. A detected image and a stored image are aligned in an alignment circuit 6a and a difference in images between the aligned detected image and stored image is detected with a difference or subtraction image detection circuit 6b. A defect is detected by binarizing the detected difference image in a binarization circuit 6c. With the above arrangement, a defect 8d existing in the detected image can be detected. As an example of devices of this type is described in SPIE Vol. 772, Optical Microlithography 6 (1987), pp. 247 to 255.

In the prior art systems, a defect is detected by finding an unmatched point between corresponding patterns, so that the detected defect has to be observed with other observation apparatus, for example, an optical microscope or a SEM to identify the kind of the defect such as deformation defect, a discoloration defect or a foreign matter defect.

SUMMARY OF THE INVENTION

It is therefore a object of the present invention to provide a defect detection method and system for a pattern to be inspected in which a defect such as a foreign matter defect, a discoloration defect and/or a deformation defect can be detected automatically in the pattern such as an LSI wafer pattern.

Another object of the present invention is to provide a defect detection method and system for a pattern to be inspected in which a fatal defect and an insignificant defect can be discriminated in the pattern such as an LSI wafer pattern.

In accordance with the present invention, a defect detection system and method for a pattern to be inspected comprises an image pickup for picking up multiple-focus images of the pattern and a defect detection arrangement for detecting a defect existing on the pattern by comparing signals of the multiple-focus images picked up with the image pickup and corresponding signals of a reference pattern.

According to a feature of the present invention, a defect detection arrangement is provided for detecting the kind of defect existing on the pattern based on signals of the multiple-focus images picked up with the image pickup.

According to another feature of the present invention, the signals of the multiple-focus images of the pattern to be tested and signals of multiple-focus images of a corresponding reference pattern having no defect are picked up by the image pickup, and a detection arrangement is provided for detecting the kind of defect existing on the pattern to be tested by comparing signals of the multiple-focus images with each other.

The present invention also provides a defect detection system and method for a pattern to be tested which comprises an image pickup for picking up multiple-focus images of the pattern to be tested and multiple-focus images of a corresponding reference pattern having no defect, a defect detection arrangement for detecting a defect by comparing at least some image signals in the multiple-focus image signals picked up with the image pickup to determine an unmatched point, a foreign matter defect detection arrangement for detecting a defect detected with the defect detection arrangement as a foreign matter defect based on a difference or subtraction image signal obtained by comparing multiple-focus image signals with each other, and a discoloration defect detection arrangement for detecting a defect detected with the defect detection arrangement as a discoloration defect based on a difference signal obtained by comparing differentiated signals with each other obtained from differential processing of the image signals.

According to the present invention a defect detection system and method for a pattern to be inspected includes a first image pickup for picking up an image of a pattern and an image of a corresponding reference pattern having no defect, a defect detection arrangement for detecting a defect by comparing image signals picked up with the first image pickup to determine an unmatched point, a second image pickup for picking up multiple-focus images of the pattern to be inspected and multiple-focus images of a corresponding reference pattern having no defect, a foreign matter defect detection arrangement for detecting a defect as a foreign matter defect based on a difference image signal obtained by comparing the multiple-focus image signals with each other, and a discoloration defect detection arrangement for detecting a defect as a discoloration defect based on a difference signal obtained by comparing differentiated signals with each other obtained from differential processing of the above-mentioned images.

The present invention according to a feature thereof, provides a defect detection system and method for a pattern to be inspected including an image pickup for picking up multiple-focus images of the pattern, multiple-focus images of a corresponding reference pattern having no defect, an optically differentiation-processed image of the pattern to be inspected, and an optically differentiation-processed image of the corresponding reference pattern having no defect; a defect detection arrangement for detecting a defect by comparing at least some image signals in the multiple-focus image signals to determine an unmatched portion; a foreign matter defect detection arrangement for detecting a defect as a foreign matter defect based on a difference image signal obtained by comparing multiple-focus image signals with each other; and a discoloration defect detection arrangement for detecting a defect as a discoloration defect based on a difference signal obtained by comparing differentiated signals with each other obtained.

The present invention also provides a defect detection system and method for a pattern to be inspected which includes an image pickup for picking up an image of the pattern to be inspected, a defect detection arrangement for detecting a defect by comparing an image signal picked up by the image pickup and a reference pattern signal; a foreign matter defect detection arrangement for detecting a defect as a foreign matter defect based on the image signal picked up; a deformation defect detection arrangement or a discoloration defect detection arrangement for detecting a defect detected as a deformation defect or a discoloration defect based on the image signal picked up; a storage arrangement for storing the information on a foreign matter defect detected with the foreign matter defect detection arrangement and the information on a deformation defect or a discoloration defect detected with the deformation defect detection arrangement or discoloration defect detection means corresponding to the position on the pattern to be inspected of a defect detected; and a comparison arrangement for comparing the information on a foreign matter defect and the information o a deformation defect or discoloration defect at the same position on the pattern to be inspected in reading out the pieces of information indicative of the defects from the storage means.

The present invention further provides a defect detection system and method for a pattern to be inspected including an image pickup for picking up a bright field image of the pattern to be inspected, a bright field image of a corresponding reference pattern having no defect, a dark field image of the pattern to be inspected, and a dark field image of the corresponding reference pattern having no defect; a defect detection arrangement for detecting a defect by comparing bright field image signals to determine an unmatched point; a deformation defect detection arrangement or a foreign matter defect detection arrangement for detecting a defect as a deformation defect or a foreign matter defect based on a difference signal obtained by comparing bright field images with each other; and a discoloration defect detection arrangement for detecting a defect as a discoloration defect based on a difference signal obtained by comparing dark field images with each other.

The above and other objects, features, and advantages of the present invention will become more apparent from the following description when taken in connection with the accompanying drawings which show, for the purposes of illustration only, several embodiments in accordance with the present invention.

BRIEF DESCRIPTION OF THE DRAWINGS

FIG. 10(a-b) show second order differentiation circuits of the system of FIG. 1;

FIG. 11 is a flow chart for processing utilizing the system of FIG. 4;

FIG. 14 shows an embodiment in which defect detection and defect classification are performed with different optical systems;

FIG. 20 shows a different embodiment for dark field image detection for determining contaminants;

DETAILED DESCRIPTION OF THE PREFERRED EMBODIMENT

The present invention utilizes the following features for inspecting a pattern:

(1) Multiple-focus images (variable density or gray scale images) are detected and compared with each other by moving a wafer to a detected defective portion and to a corresponding nondefective portion and moving the wafer up and down (Z direction) or utilizing multiple image pickups having different focal positions, a detection arrangement for detecting circuit pattern images in a plurality of Z positions and a storage arrangement for storing detected images.

(2) A foreign matter defect is judged with a detection arrangement for detecting the density change in the Z direction on a difference image obtained by comparing variable density images at a defective portion and a nondefective portion in each Z position.

(3) On a focal plane, detected variable density images in a defective portion and in a nondefective portion are compared after spatial differentiation, and a discoloration defect is judged with a detection arrangement which detects a density variation of a difference image depending on the differentiation order.

(4) Foreign matter or contaminant defects and discoloration defects are judged successively in this order with the aforementioned detection arrangements, and the remainder of the defects are judged to be deformation or pattern defects.

Figure 1:
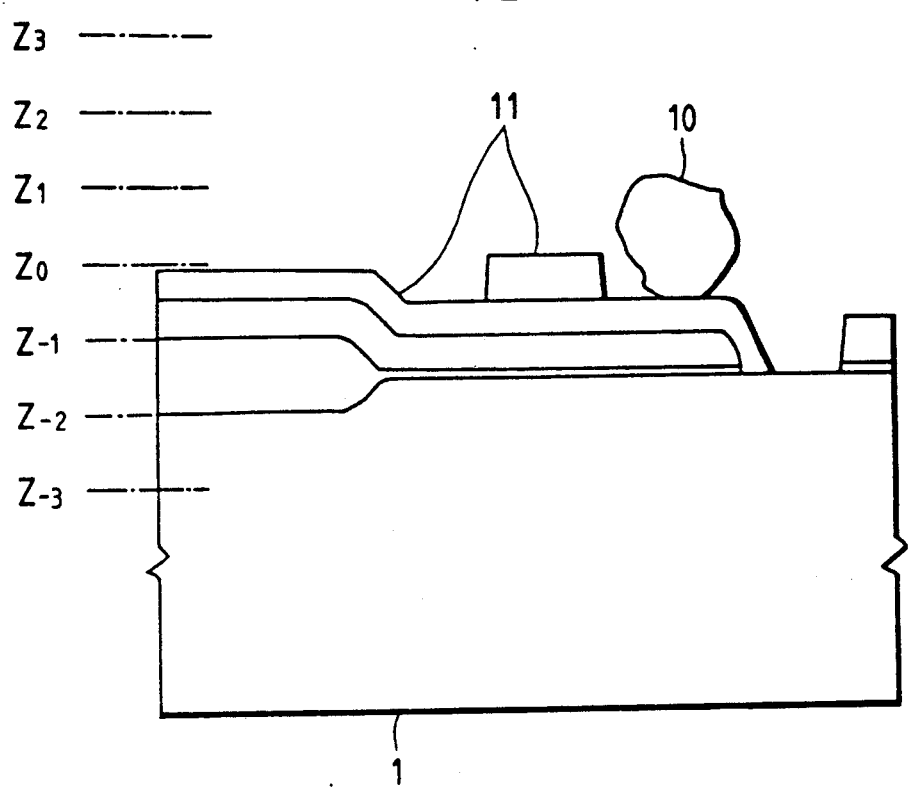
FIG. 1 shows the relation between a pattern to be inspected and Z focal point positions.
Figure 2:
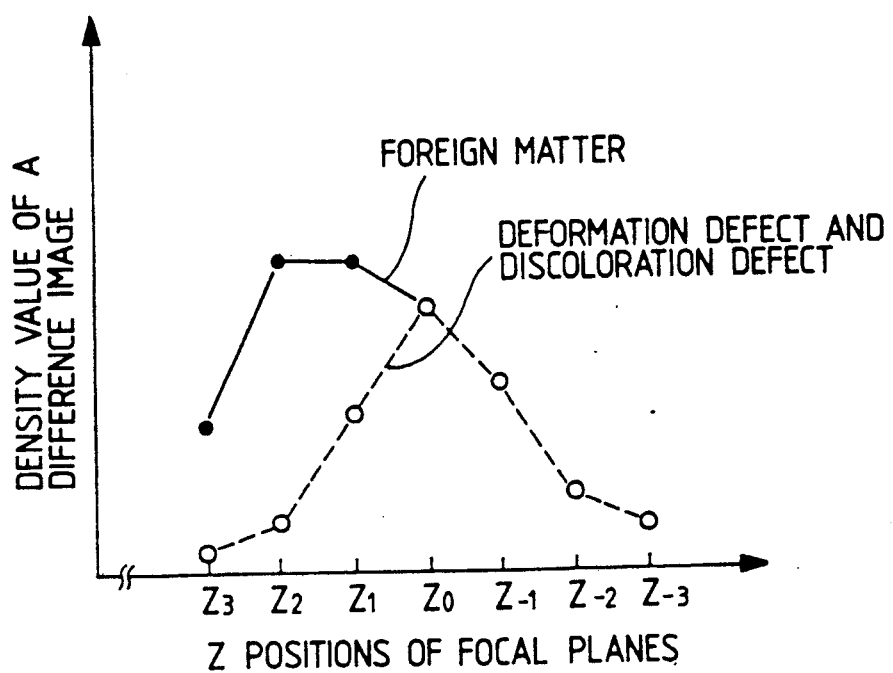
FIG. 2 shows the relation between a Z position on a focal plane and a density value of a difference image in each defect.

Referring to FIG. 1 of the drawings, a circuit pattern 11 on a wafer 1 to be inspected is illustrated, and multiple-focus images are detected at a plurality of points $Z_3$, $Z_2$, $Z_{-3}$, which are located apart from each other on a straight line in Z direction through the focal point $Z_0$ on the upper side and lower side of ZO. Therefore the image detected at $Z_0$ is in focus for the circuit pattern 11 (pattern to be inspected), but the images at $Z_1$, $Z_2$ or $Z_3$ are out of focus and the images of the circuit pattern 11 are blurred. A foreign matter or contaminant 10 such as a piece of dust, etc. is shown on the circuit pattern 11, so that the image of the foreign matter can be still in focus at $Z_1$. This is the point to which attention is to be paid. When Z positions of focal planes are expressed on the axis of abscissas and density or gram scale values in a gradation of difference images between the images at a defective portion and a nondefective portion are expressed on the axis of ordinates, a foreign matter or contaminant defect has a different waveform from that of a deformation or pattern defect or of a discoloration defect, so that a foreign matter defect can be discriminated as shown in FIG. 2.

Figure 3:
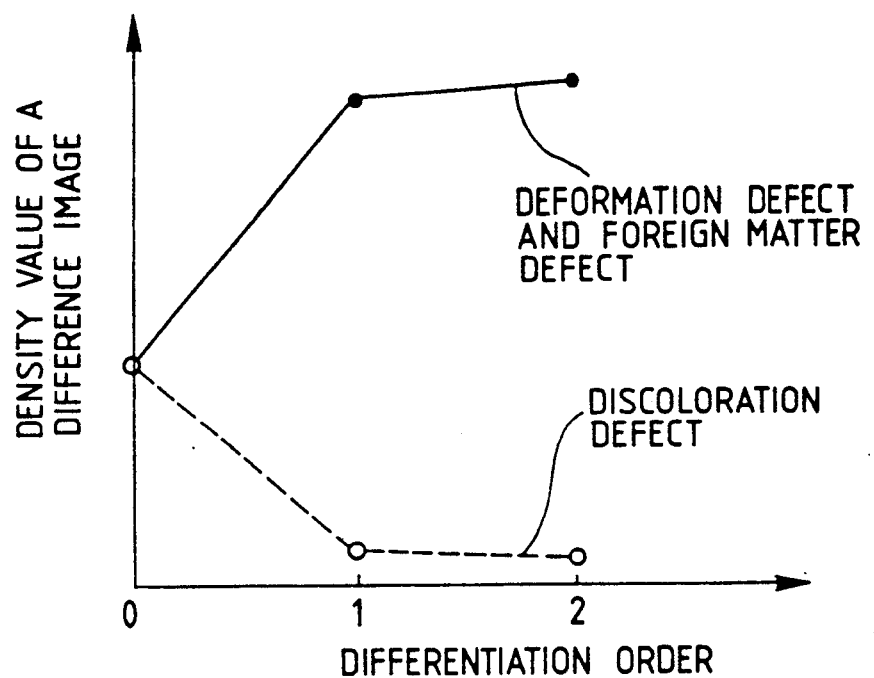
FIG. 3 shows the relation between the order of differentiation and a density value of a difference image.

When a variable density image detected on a focal plane $Z_0$ is spatially-differentiated, in the case of discoloration defect a DC component predominates, so that the density of a difference image of differentiated images becomes small as compared with that of a deformation defect or of a foreign matter defect. Assuming that the axis of abscissas expresses the order of differentiation, that is a first order differentiation and a second order differentiation (a zero order differentiation being indicative of no differentiation), and the axis of ordinates expresses the density values of difference images, then a discoloration defect takes a different waveform from that of a deformation defect or a foreign matter defect as shown in FIG. 3. Thereby a discoloration defect can be discriminated.

Defects other than foreign matter defects and discoloration defects discriminated by waveform analysis are considered to have some defects in the shape of a circuit pattern and they are judged to be deformation or pattern defects.

Tests or inspections are performed before and after the processing of a pattern to be inspected with a manufacturing device etc., and when a defect is detected in the same place on the pattern in both cases, i.e., before and after processing and if the defect is detected as a foreign matter defect in the before-process test and detected in the after-process test as a deformation defect or a discoloration defect the defect is discriminated (classified) as a fatal defect. These fatal defects are properly removed or patterns with them are not utilized so as to enable reliable manufacture of IC's and LSI'S.

An embodiment of the present invention described with reference to FIG. 4 wherein a circuit pattern to be inspected on the wafer 1 is illuminated by a Xe lamp 12 and is enlarged and detected with a TV camera 13 through an object lens 3. The output of the TV camera is converted to a digital signal with an A/D converter 14. Any photoelectric converter such as a TV camera or linear image sensor can be used. In the case of a linear image sensor, a two dimensional pattern on a wafer is detected with the self-scanning operation and an xy table which moves at a right angle to the direction of the self-scanning operation. The detected variable density or gray scale image is compared with the image of the preceding chip stored in an image memory 15b for the judgment of a defect. In other words a defect is detected, as shown in FIG. 5, by detecting a circuit pattern in a position 7d inside a chip 7 and comparing the detected circuit pattern image signals with a circuit pattern image signals in a position 7c, which is a position corresponding to that of the adjacent chip previously detected and stored in the image memory 15b.

Figure 4:
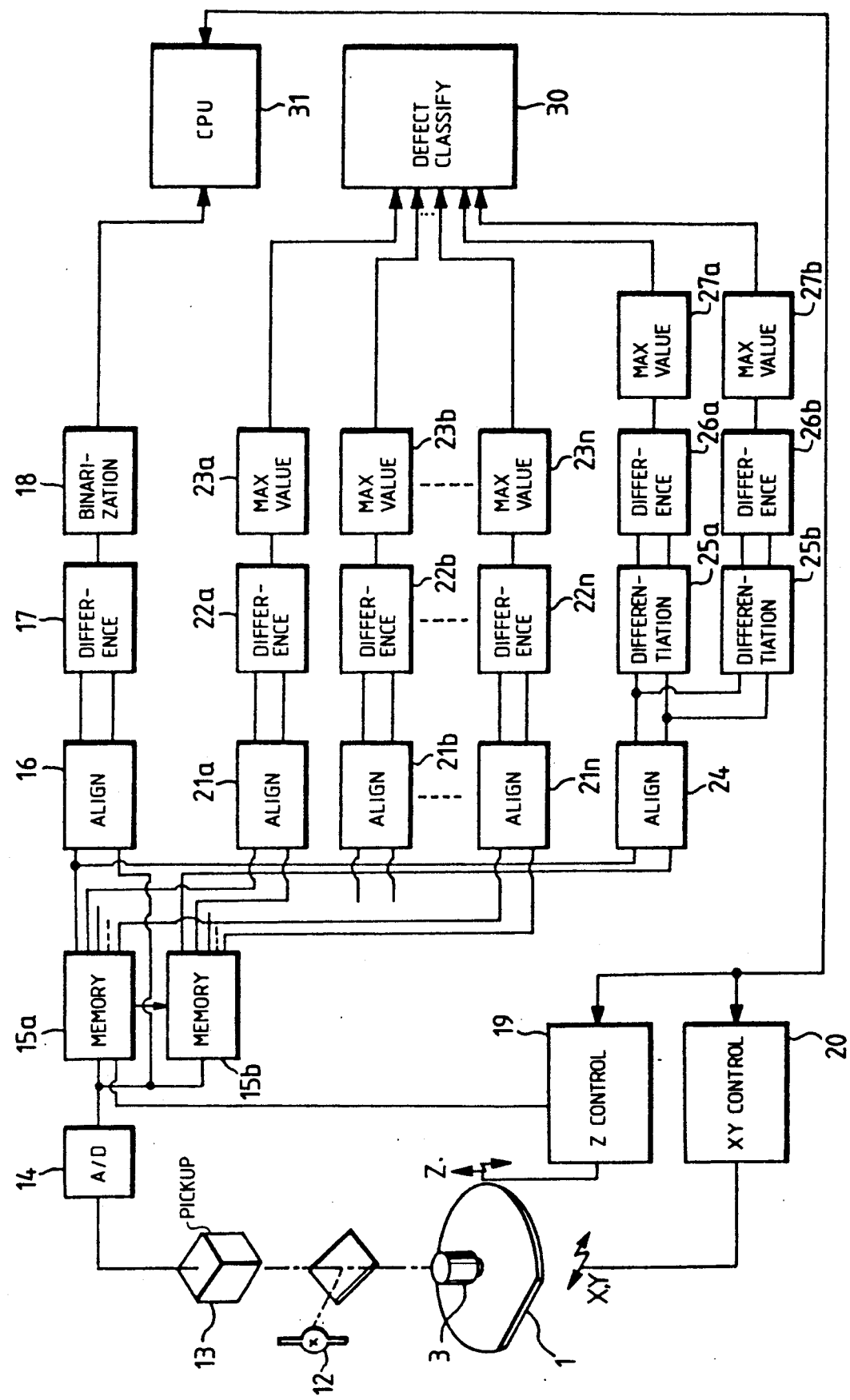
FIG. 4 shows an embodiment of a defect detection system for a pattern to be inspected according to the present invention.
Figure 6E:
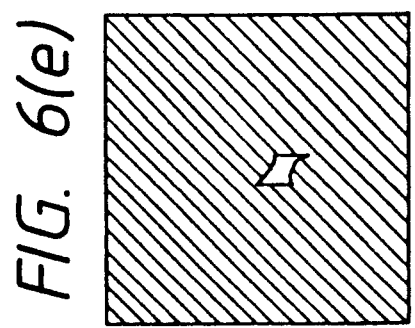
FIGS. 6(a-e) show a detected image, a stored image, aligned images, a difference image and a binarized image, respectively, obtained in the system of FIG. 4.
Figure 6D:
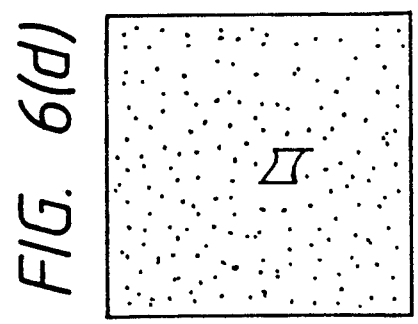
Figure 6C:
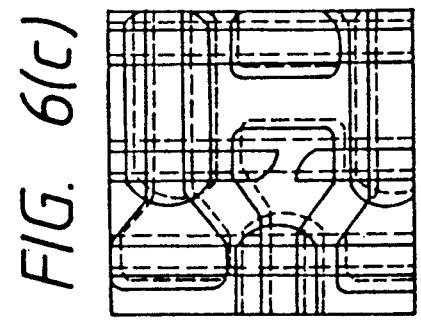
Figure 6A:
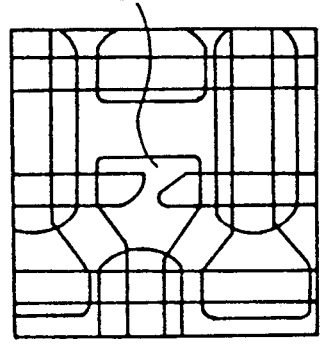
Figure 6B:
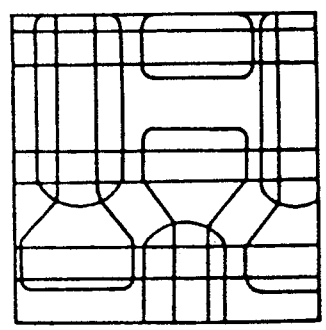
Figure 7D:
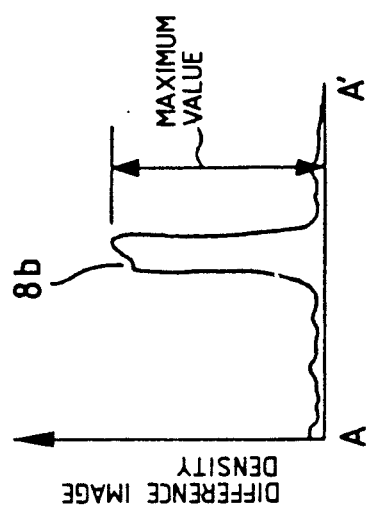
FIGS. 7(a-d) show a defective portion image and a nondefective portion image at $Z=Z_1$, a difference image obtained in aligning the two images and a density value waveform of the difference image, respectively, obtained in the system of FIG. 4.
Figure 7C:
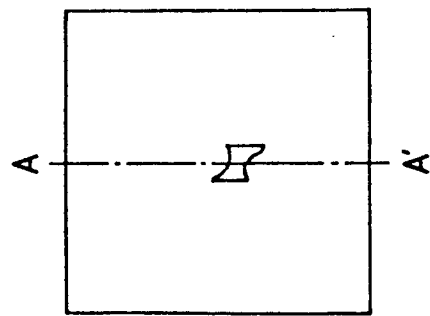
Figure 7A:
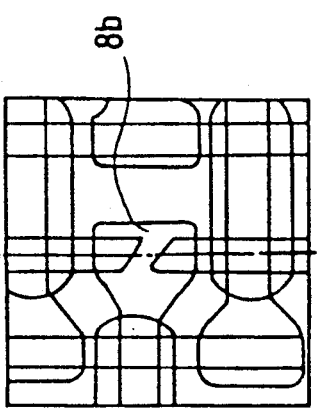
Figure 7B:

At first, a detected image, FIG. 6(a), and a stored image, FIG. 6(b), are aligned, FIG. 6(c) in an alignment circuit 16 shown in FIG. 4, and a difference image between the aligned detected image and stored image is detected. FIG. 6(d), with a difference image detection circuit 17 shown in FIG. 4. A binary image, FIG. 6(e), is obtained by binarizing the difference image signal in a binarization circuit 18 as shown in FIG. 4. In this way, pattern breakage 8b existing in the detected image, FIG. 6(a), is detected as a defect. The image obtained by detecting a circuit pattern in a position 7d is newly stored in the image memory 15b and is used for the test in a position 7e, the position of the next chip.

Figure 5:
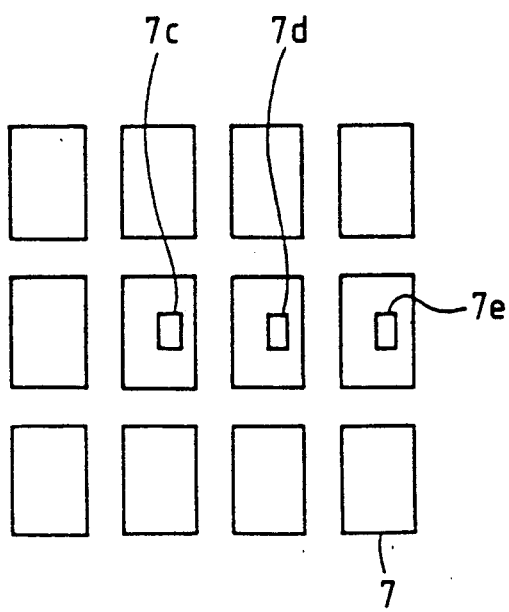
FIG. 5 shows a state where circuit patterns in the positions inside adjacent chips on a wafer are compared in the system shown in FIG. 4.

In FIG. 5, if a defect is in the position 7d the defect can be detected in the comparison between the patterns in the 7c and the 7d positions and also between patterns in the 7d and the 7e positions, so that in collating individual two-chips-comparison results with each other the location of the defect can be specified. The collation is performed with a CPU 31 shown in FIG. 4.

When a defect is judged to be in the 7d positions with the signal from the binarization circuit 18, the wafer is moved with a Z control circuit 19 which moves the wafer up and down to detect the images of the defective portion 7d in individual Z positions and these images are stored in the image memory 15a. The movement of a wafer in xy direction is effected by a xy control circuit 20, and a wafer is moved to a nondefective portion corresponding to the defective portion, for example, to the position 7c and the images of the nondefective portion are detected at individual Z positions in the similar manner to the case of the defective portion 7d, and these images are stored in the image memory 15a. A defective portion image at $Z=Z_1$ stored in the image memory 15a is aligned with a nondefective portion image at $Z=Z_1$ stored in the image memory 15b in an alignment circuit 21a. A difference image between the aligned images is detected with a difference image detection circuit 22a and the density value at a defective portion of a difference image is detected with a maximum value detection circuit 23a.

These processes are shown in FIG. 7. A difference image, FIG. 7(c) is obtained by aligning a defective portion image, FIG. 7(a) and a nondefective portion image, FIG. 7(b). A maximum value of density in the difference image, FIG. 7(c) is detected with the maximum value detection circuit 23a, FIG. 7(d). The density difference between the defective portion 8b and the nondefective portion is so large that the density difference between the defective portion 8b and the nondefective portion can be detected with the maximum value detection circuit 23a.

In similar manner, the images of a defective portion and a nondefective portion at $Z_2$ to $Z_n$ positions stored in the image memories 15a and 15b are aligned in the alignment circuits 21b to 21n, and the difference images are detected with image detection circuits 22b to 22n, and the density values of the difference images at defective portions are detected with the maximum value detection circuits 23b to 23n. For example, $2n+1$ sheets of variable density images having picture elements of $1024 \times 1024$ are stored in each of these image memories 15a and 15b.

The image memory 15a, in addition to storing multiple focus images, has a storage capacity for storing a sheet of variable density image to be used for ordinary defect judgment. Owing to this function, it is made possible to realize a sequence control in which defect judgment and defect classification can be made alternately as described later.

A defective portion image and a nondefective image at $Z=Z_0$ are aligned in a alignment circuit 24, and the first order derivatives of these images are obtained with a first order differentiation circuit 25a, and the difference image therebetween is detected with a difference image detection circuit 26a, and then the density value of the defective portion in the difference image is detected with a maximum value detection circuit 27a. In a similar manner, the second order derivatives of a defect portion image and a nondefective portion image are obtained in a second order differentiation circuit 25b, and a difference image therebetween is detected with a difference image detection circuit 26b, and then the density value of the difference image is detected with a maximum value detection circuit 27b.

All of these detected values are input to a defect classification circuit 30. The defect kind judgment is made in the defect classification circuit 30 based on FIG. 2 and FIG. 3 in accordance with the flow chart of FIG. 8, which processing is obtained by software.

Referring to FIG. 4, a lens having shallow focus depth, a high resolution characteristic and a large value of NA such as 0.8 to 0.95 is selected for the object lens 3. When a defect is detected, utilizing the object lens of shallow focus depth, images are detected moving a wafer up and down, for example, at intervals of 0.2 μm; among these images only one image on a certain plane is in focus. When the images are detected in the range of 0.6 μm, seven different focal plane images are detected, i.e., $Z_3, Z_1 \ldots Z_{-3}$. The alignment between a defective portion image and a nondefective portion image is performed in the alignment circuit 16, 21a to 21n, and 24. This alignment can be effected in the manner described in The Technical Journal Vol. 87, No. 132, pp 31 to 38 of The Institute of Electronics and Communication Engineers of Japan. After the detection of difference images of seven pairs of aligned images, the density values of the difference images are detected; in the case where a defect is a foreign matter defect, the density values at $Z_1$ and $Z_2$ located on the upper side of a focal plane $Z_0$ are still comparatively large as shown in FIG. 2, so that the defect can be easily judged if it is a foreign matter defect in the classification circuit 30, for example by following the flow chart shown in FIG. 8.

Figure 9:
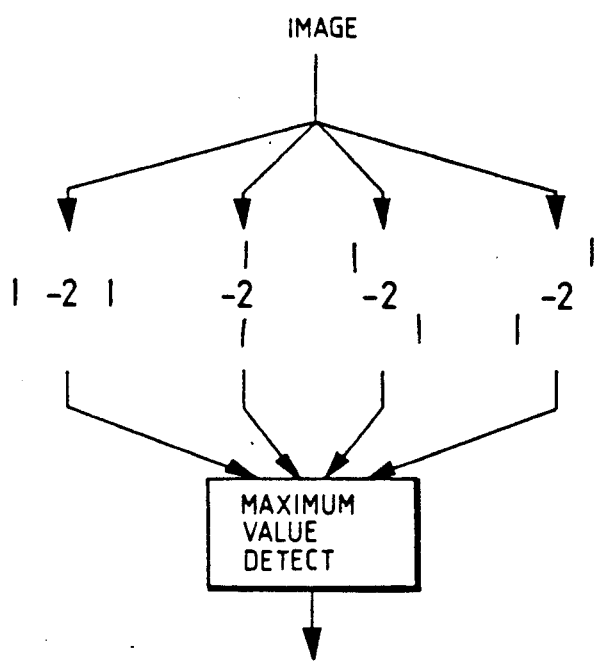
FIG. 9 shows the image differentiation processing performed with the differentiation circuit shown in FIG. 1.

Differentiation of an image is performed in a differential circuit 25; second order differentiation of an image is realized by processing the image with four kinds of edge operators (1, −2, 1) and by detecting the maximum value as shown in FIG. 9 and as described in U.S. Pat. No. 4,791,586.

A second order differentiation circuit 25b is shown in FIG. 10. In FIG. 10(a), for example, an 8 bit digital image signal from the alignment circuit 24 is received in a three stage shift register 250; the output of the first stage and the third stage is supplied to an adder 251 and the output of the second stage is supplied to an amplifier 252 having a gain of two. The output of the adder 251 and the output of the amplifier 252 are supplied to a subtracter 253. An operator of "1, −2, 1" is constituted by the shift register 250, the adder 251, the amplifier 252 and the subtracter 253.

FIG. 10(b) shows a circuit for differentiation in three directions, a longitudinal direction, a horizontal direction and a diagonal direction; the output of the aligning circuit 24 is supplied to a $3 \times 3$ slicing circuit 254, and three picture elements of a longitudinal direction, a horizontal direction and a diagonal direction are selected and they are supplied to four operators OPI to OP4 to differentiate an image signal. Each operator can be similar to that shown in FIG. 10(a). The output of these four operators is supplied to a maximum value detection circuit 255 and the maximum value among such outputs is selected.

After differentiation a difference image is detected with the density value having a waveform as shown in FIG. 3. In the case of a discoloration defect the density value is small, so that it can be easily judged if the defect is a discoloration defect with the defect classification circuit 30 following the flow chart shown in FIG. 8. It is recognized that such discoloration defect determination is independent of the illumination light wavelength.

A process flow is shown in FIG. 11. The axis of abscissas expresses time. A test is made repeatedly in performing image detection and defect judgment as shown in part (a). Image detection is made with a TV camera 13, an A/D converter 14 and an image memory 15a as shown in FIG. 4, and defect judgment is made with an alignment circuit 16, a difference image detection circuit 17, a binarization circuit 18 and a CPU 31 which specifies a defect position. When a defect is detected, the above-mentioned testing is suspended and multiple-focus images of a defect portion and a corresponding nondefective portion are detected as shown in part (b). This image detection is made with the TV camera 13, A/D converter 14 and image memories 15a and 15b. In the next step, the difference images of these images and the maximum value are detected. These processes are realized with alignment circuits 21a, . . . , 21n, and 24; difference image detection circuits 22a, . . . , 22n, 26a and 26b; differentiation circuits 25a and 25b; and maximum value detection circuits 23a, 23n, 27a and 27b. When all the maximum values of images and the maximum values of difference images of differentiated images at each Z position are detected, defects are classified into foreign matter defects, discoloration defects or deformation defects with the defect classification circuit 30. And again image detection and defect judgment ar repeatedly performed until a defect is detected as shown in part (a').

Figure 12:
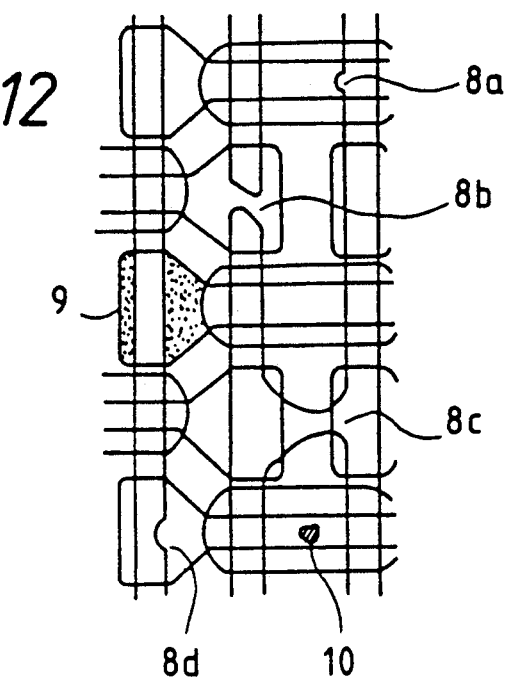
FIG. 12 shows various kinds of defects existing on a pattern to be inspected.

The defects existing on a test object pattern on a wafer are shown in FIG. 12. Detection object defects to be found on a circuit pattern are deformation or pattern defects 8 such as swell out defects 8a, breakage defects 8b, short-circuit defects 8c or chipped off defects such as notches 8d, discoloration defects 9 or foreign matter or contaminant defects 10.

Figure 13:
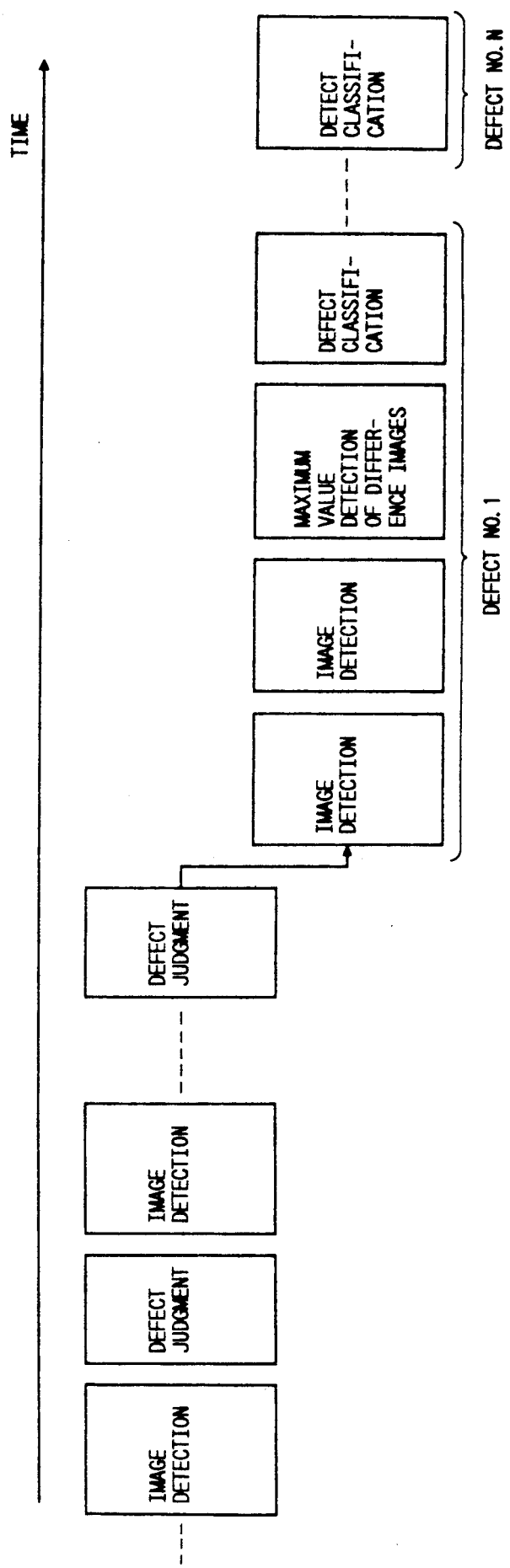
FIG. 13 is a flow chart for processing different from that shown in FIG. 11.
Figure 16:
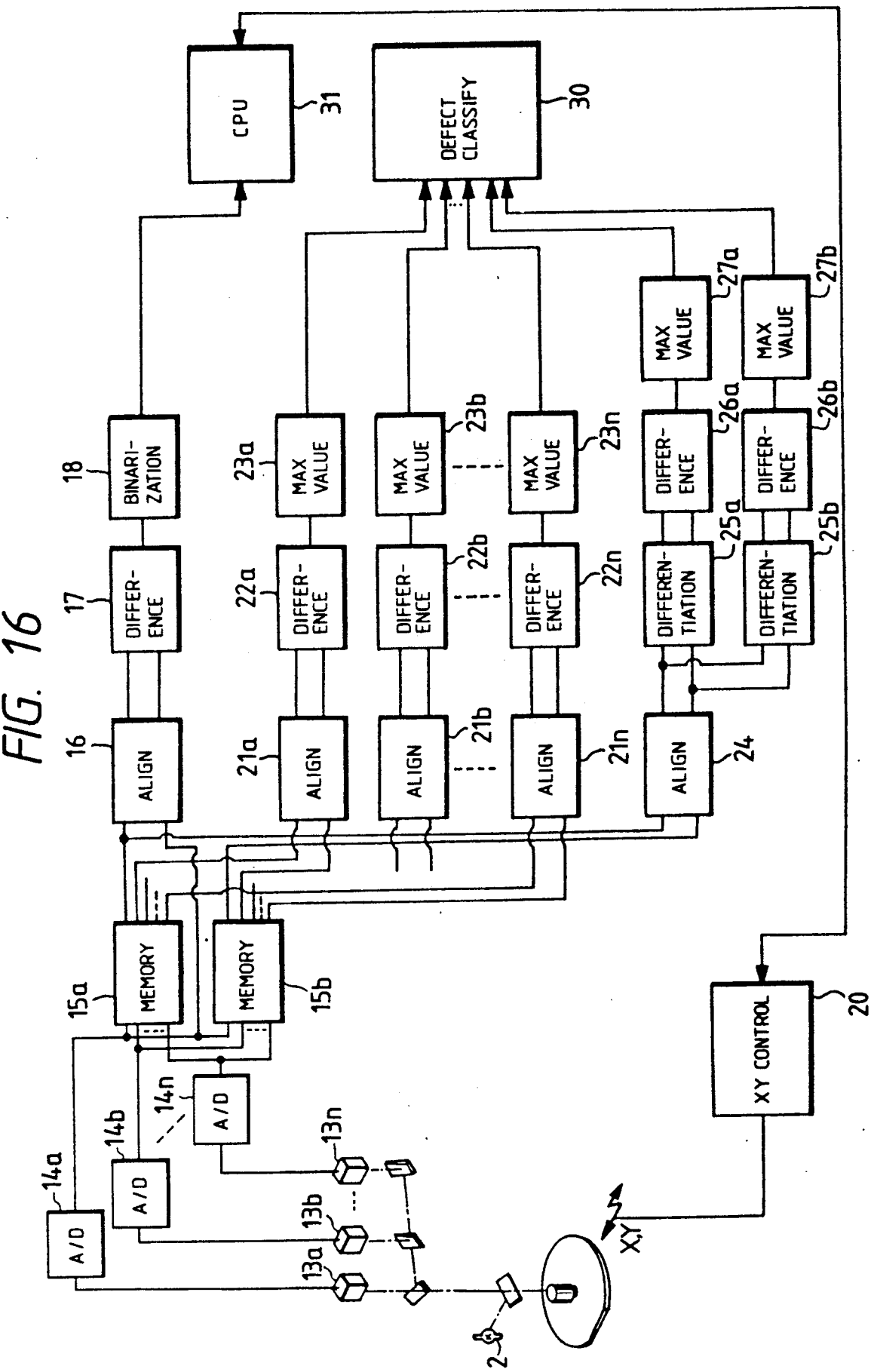
FIG. 16 shows another embodiment of the present invention utilizing the pickup of FIG. 15.

The above explanation has been directed to a sequence is explained in which in each case when a defect is detected classification is made, but another sequence as shown in FIG. 13 can be used, for example, in which all the defects on a wafer are detected and the position coordinates thereof are stored in the CPU 31, and after the testing, defect classification is effected by reading out the defects successively from the memory.

It is also possible to perform defect detection and defect classification in different optical system for performing defect detection at a high speed with low magnification and defect classification accurately with high magnification as shown in FIG. 14, the various parts being designated by like reference numerals as utilized in FIG. 4. Any type of illumination device may be utilized. Generally, inspection is carried out at high speed which necessitate an object lens 31 of lower magnification and which when utilized in an inspection system enables detection of existence of defects, but which has insufficient resolution to enable classification of defects. That is, when a defect is classified as described in connection with FIG. 4, the object lens 3 has high resolution. For example, if a high N.A. (Numerical Aperture) object lens, i.e., a high magnification lens is utilized, the multiple-focus images can be readily obtained due to the shallow focal depth thereof and such multiple-focus images are utilized for defect classification. By utilizing the two systems as shown in FIG. 14, lower magnification with object lens 3' for defect detection at high speed and higher magnification with object lens 3 for defect classification at lower speed only a small amount of additional time is required since the classification is conducted only for the previously detected defects. Thus, the total inspection time for classification of defects is reduced. In FIG. 14, the object lens may be exchanged after defects are detected, and then the defects are classified. With exchange of the object lens, the lamp 12 and the TV camera are utilized in common.

Figure 15:
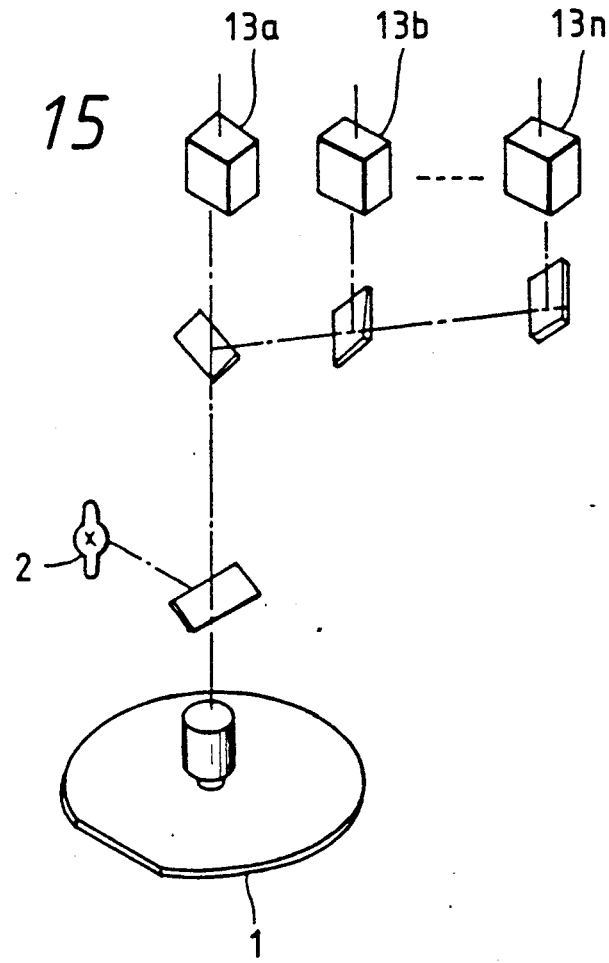
FIG. 15 shows another embodiment of a multiple-focus image pickup.

FIG. 15 shows another embodiment of multiple-focus image pickup. With this image pickup, it is possible to simultaneously obtain a plurality of images having focal planes at $Z_3, \ldots, Z_{-3}$ by setting a plurality of TV cameras 13a, 13b, ... in an optical path apart from each other and with different focal positions, thereby avoiding movement of wafer 1 up and down with Z control circuit 19.

Figure 8:
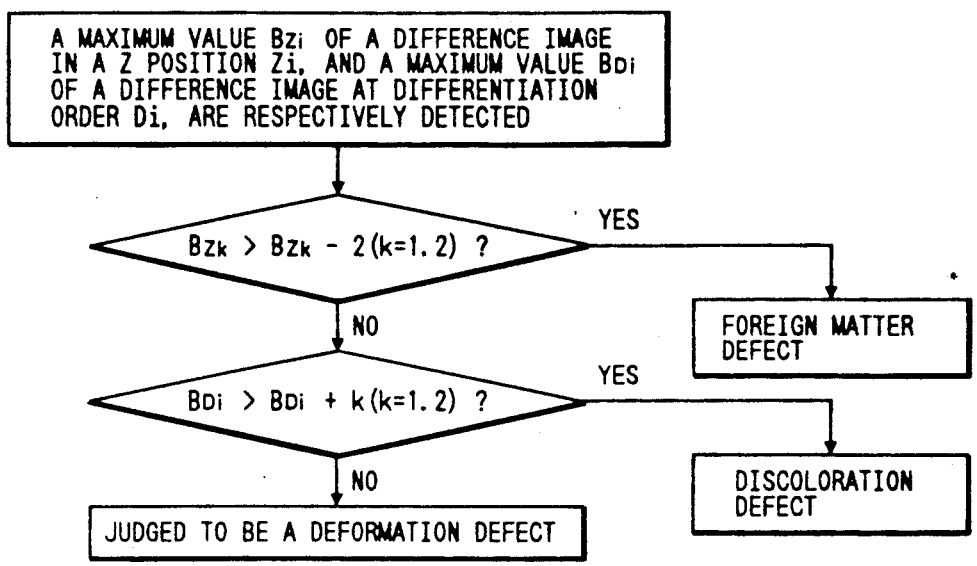
FIG. 8 is a flow chart for the judgment of the kind of defect with the defect classification circuit of the system of FIG. 1.

FIG. 9 shows the system utilizing the pickup of FIG. 8 wherein an image in focus is obtained with the camera 13a and is input to the image memory 15a to be used for defect judgment and also input to the alignment circuit 16 through the A/D converter 14a. When defects are being classified, all images obtained with cameras 13a to 13n are input simultaneously to the image memories 15a and 15b. Therefore, the image memories have the capacity to be able to write n sheets of images simultaneously. In reading however, it is sufficient that an image can be read from the memory one sheet by one sheet.

In FIG. 4 an image is differentiated for judging a discoloration defect, but it can be judged with other circuit constructions. As described in the book, "Methods of Image Pattern Recognition" pp. 17 and 18 published by Corona Inc., an edge of a circuit pattern can be emphasized when Fourier transformation is applied to an image signal and after filtering, an inverted Fourier transformation is applied. Utilizing the above method, a difference image between a defective portion image and a nondefective portion image is detected and based on the magnitude of a density value a defect can be judged as a discoloration defect.

Figure 17:
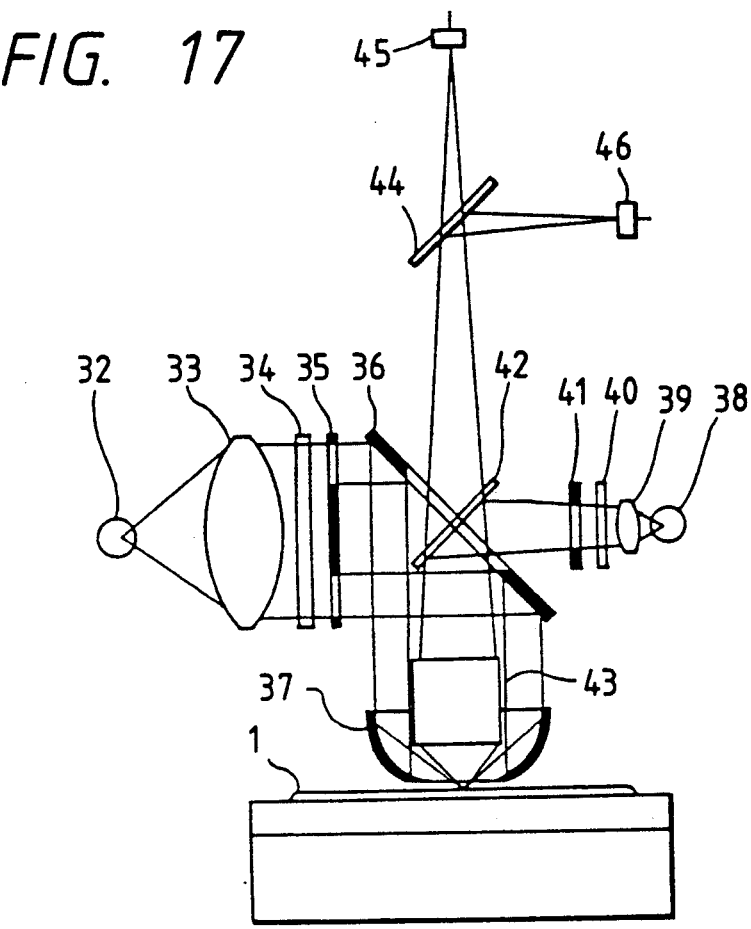
FIG. 17 shows an optical detector utilizing bright and dark field illumination.

It is also possible to discriminate a discoloration defect with an optical arrangement. As shown in FIG. 17, an image detection system is constituted with a dark field illumination system comprising a lamp 32, a condenser lens 33, a narrow band filter 34 (wavelength $\lambda_1$) for selecting the wave length for dark field illumination, a ring-shaped aperture slit 35, a ring-shaped mirror 36, and a parabolic concave mirror 37; and with a bright field illumination system comprising a lamp 38, a condenser lens 39, a wave length selecting filter 40 (wavelength $\lambda_2$), a circular aperture slit 41, a half-mirror 42, an object lens 43, a wavelength separation mirror 44, a dark field image detection TV camera 45, and a bright field image detection TV camera 46. In the above-mentioned image detection system, dark field illumination is limited to a wavelength $\lambda_1$ with the filter 34 and the light is radiated in a slant direction from surroundings onto the pattern with the concave parabolic mirror 37, and bright field illumination is limited to a wavelength $\lambda_2$ and the light is radiated onto the pattern from above. A dark field image of a defective portion and a dark field image of a nondefective portion are detected and these images are aligned in the alignment circuit 24a shown in FIG. 11 and then a difference image is detected with the difference image detection circuit 26a.

Figure 19:
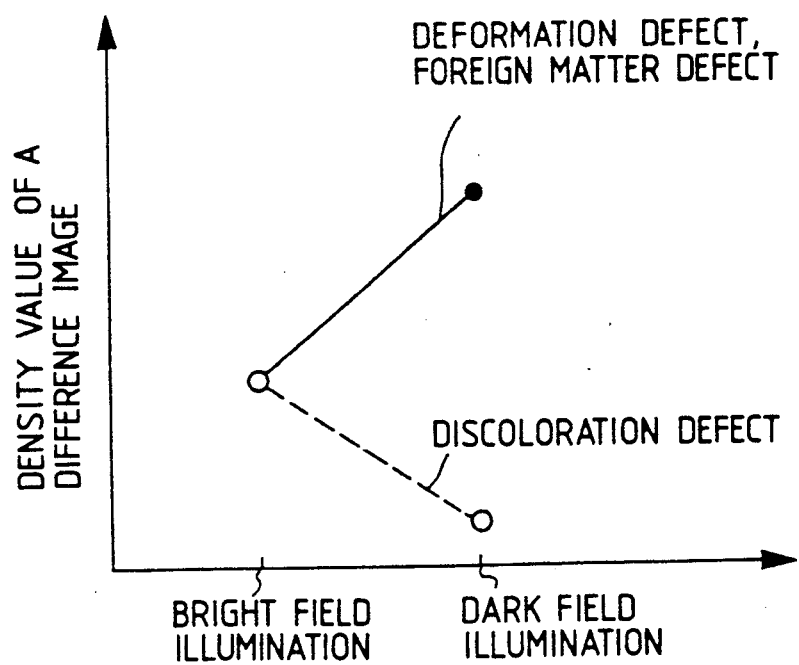
FIG. 19 shows the relations between the density values of difference images, and the bright field illumination and the dark field illumination in each kind of defect.
Figure 18:
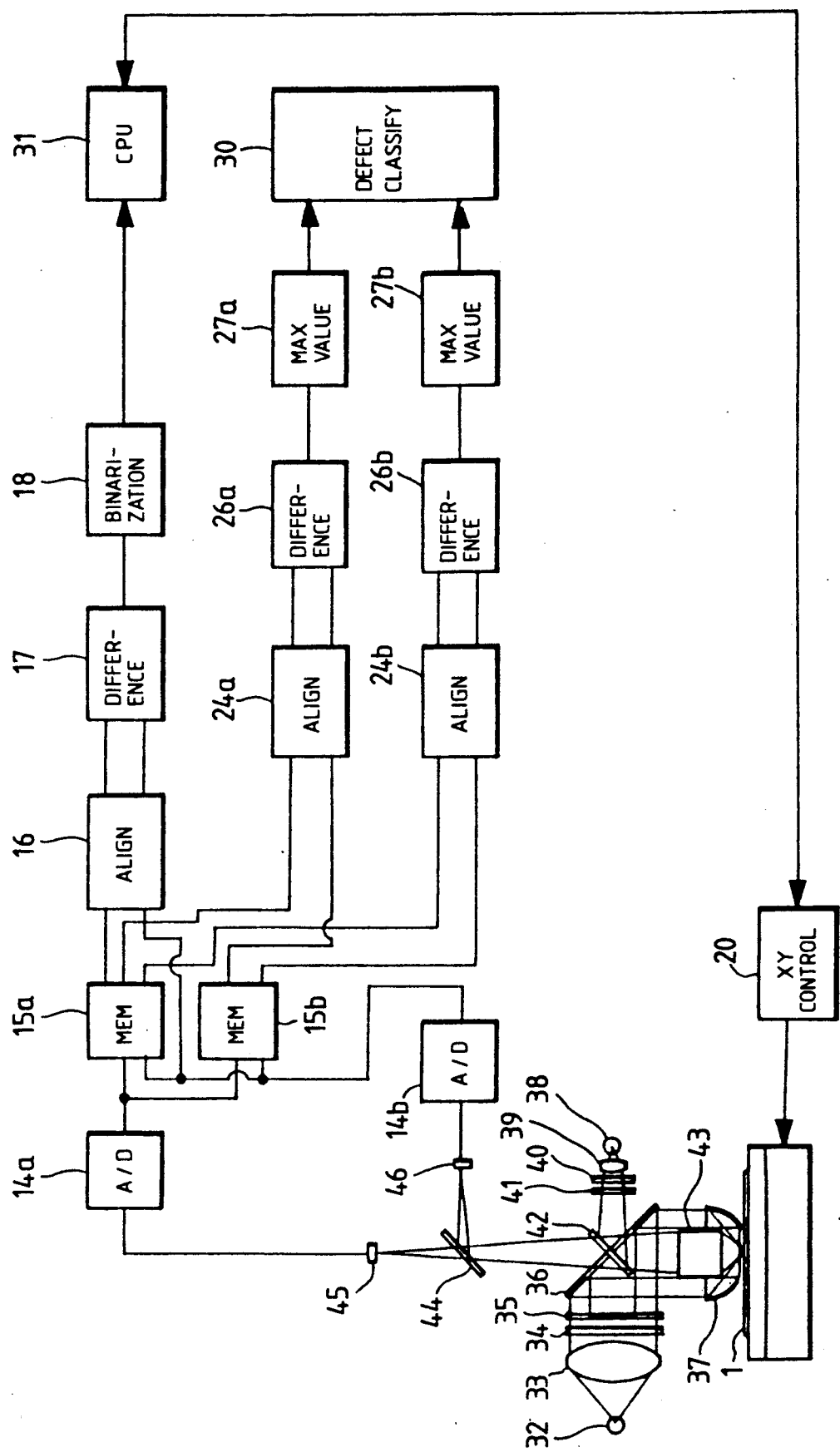
FIG. 18 shows a discoloration detection system and defect detection system utilizing an optical detector of FIG. 17.

In similar manner, a bright field image of a defective portion and a bright field image of a nondefective portion are detected and these images are aligned in the alignment circuit 24b and then a difference image is detected with a difference image detection circuit 26b. The density values of these difference images are detected in the maximum value detection circuits 27a and 27b. Then, as shown in FIG. 19, if the defect is a discoloration defect, the density value in the case of the dark field illumination is small in comparison with the case of a deformation defect or a foreign matter defect, so that the defect is easily judged to be a discoloration defect. As recognized, such discoloration defect determination is wavelength dependent. FIG. 18, the alignment circuit 16, the difference image detection circuit 17, and the binarization circuit 18 are conventional circuits used for defect judgment as shown in FIG. 4.

In FIG. 20, a detection system which can be utilized in place of the detection of dark field images is illustrated, wherein a wafer 1 is irradiated with an S polarized laser beam at an angle of $\phi$ with S polarization lasers 47a and 47b. The angle $\phi$ is about 1 degree. In this case, a laser beam which vibrates at a right angle to the plane formed with a normal line to the wafer and the radiating laser beam is called an S polarization laser beam and the beam which vibrates parallel to the plane is called a P polarization laser beam. When a circuit pattern on the wafer has low steps only, the polarization direction of the scattered light is not changed and proceeds towards an object lens 48 keeping the S polarization plane as it is as shown in solid line, but in the case where there is a foreign matter or a high step in the pattern, the polarization plane of the laser beam which impinges on the pattern is changed, so that it contains many P polarization components shown in dotted line. Therefore, the scattered light from a circuit pattern edge having a foreign matter or a high step can be detected by providing a polar screen 49 which cuts off the S polarization beam behind the object lens 48 and by detecting the light which passes through the screen with an optical element 50 such as a photomultiplier. The scattered light signal is converted to a digital signal with the A/D converter 14. The detected signal is compared with the preceding chip signal stored in the image memory 15a. These signals are aligned in the alignment circuit 16 and the difference signal is detected with the difference signal detection circuit 17. The scattered light signal from a circuit pattern edge with a high step is contained in both signals in common, so that only the scattered light signal from a foreign matter is contained in the difference signal. A defect can be detected by binarizing the difference signal with the binarization circuit 18, thereby defect detection can be performed. The aforedescribed arrangement is substantially disclosed in "The Japan Society of Applied Physics and Related Societies", March 1988, pg. 701 and is utilized to detect a defect such as a contaminant.

Figure 21:
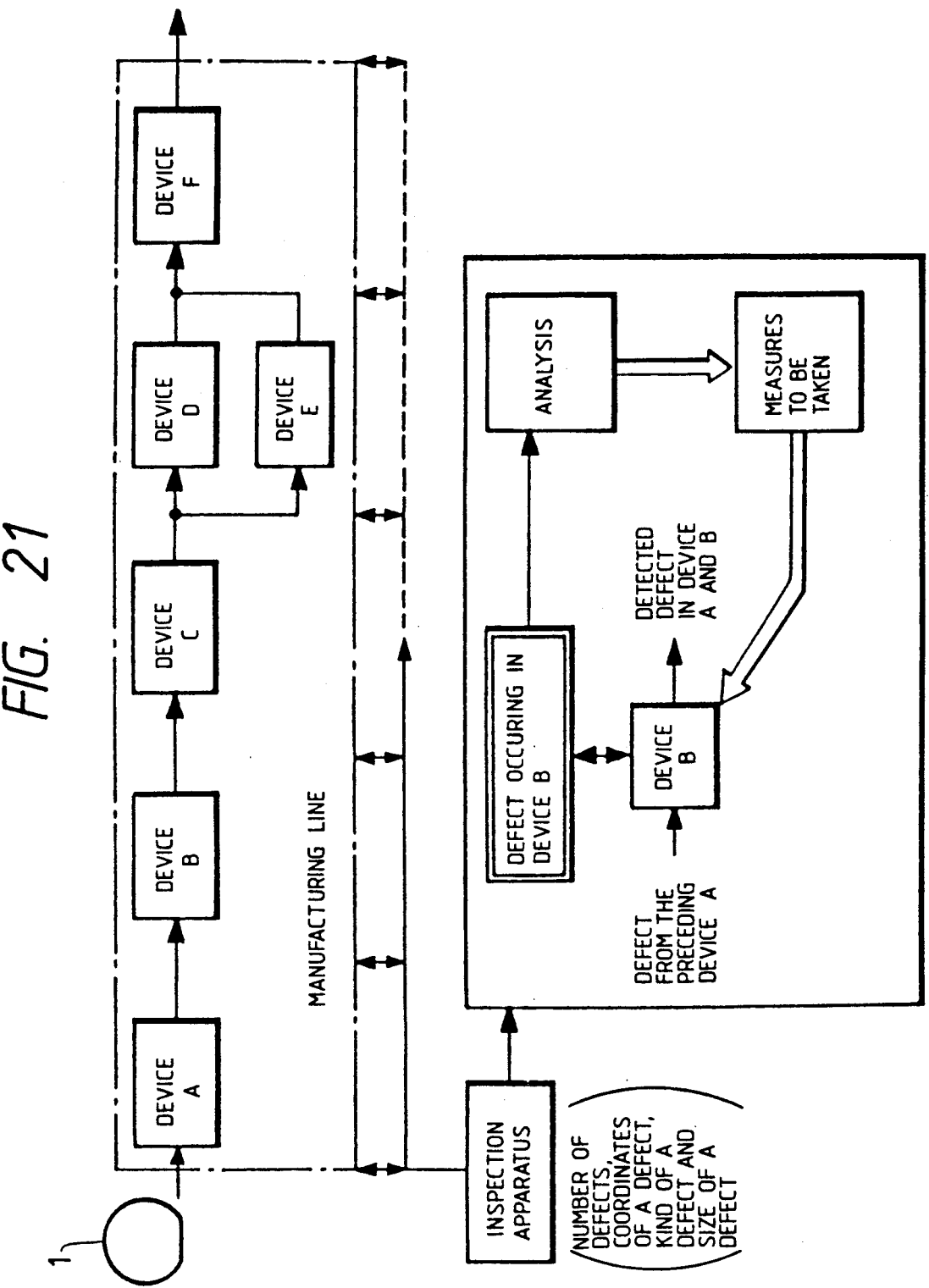
FIG. 21 shows a system for discriminating a defect which is not fatal and a fatal defect utilizing the defect detection system for a pattern to be inspected according to the present invention in a semiconductor manufacturing line.

By using the defect detection system described above, it is also possible to realize a more effective processing system which is described in the following. As shown in FIG. 21, a semiconductor manufacturing line is provided wherein a pattern on a wafer is successively formed or manufactured by successive processing, for example, in a plurality of devices A, B . . . F, wherein the devices may be identical or different. A wafer is inspected utilizing a detection system having the construction described in the above, and in each of these devices A, B, . . . , F inspection and defect classification are performed prior to and after processing in the respective device by a test or inspection apparatus as represented by the double headed arrows. The occurrence of a defect can be examined as the wafer passes through each of these devices by checking the coordinates of the defect. For example, a defect detected in the inspection of a wafer processed in device B can be a defect originating in the preceding device A or a defect produced or occurring in the device B. It can be determined whether the defect is produced in the device B or occurred in the preceding device A by referring to the defect data obtained in the inspection when the wafer is processed in the device A. Among the defects introduced from the preceding device A, some of the foreign matter defects do not cause deformation defects or discoloration defects in the device B. That is, a pattern with a fatal foreign matter defect is without fail detected as a pattern with a deformation defect or a discoloration defect in the following device, but a pattern having no fatal foreign matter defect is not detected as a deformation defect in the following devices and is accepted as a good article. On a defect classified as a foreign matter defect by a inspection apparatus having a construction as described above, its coordinates are stored in a memory, and its fatalness can be judged by performing detection and classification of the defect again after the wafer passes through the next device as shown in FIG. 21. Thereby, it becomes possible to obtain more accurate information of the condition of a manufacturing and line accurately.

For example, if a large number of foreign matter defects occur in device A, whereas a small number of foreign matter defects occur in device C, but more fatal foreign matter defects are caused in device C than in device A, then device C is primarily responsible for reducing yield and problems in device C must be corrected. Such correction may entail cleaning or tuning of device C. That is, for manufacturing purposes, the number of defects occurring in a particular device is not important so long as the defects are not fatal foreign matter defects and with the disclosed system, the count of fatal foreign matter defects is detected and the appropriate device corrected so as to improve yield.

Figure 22:
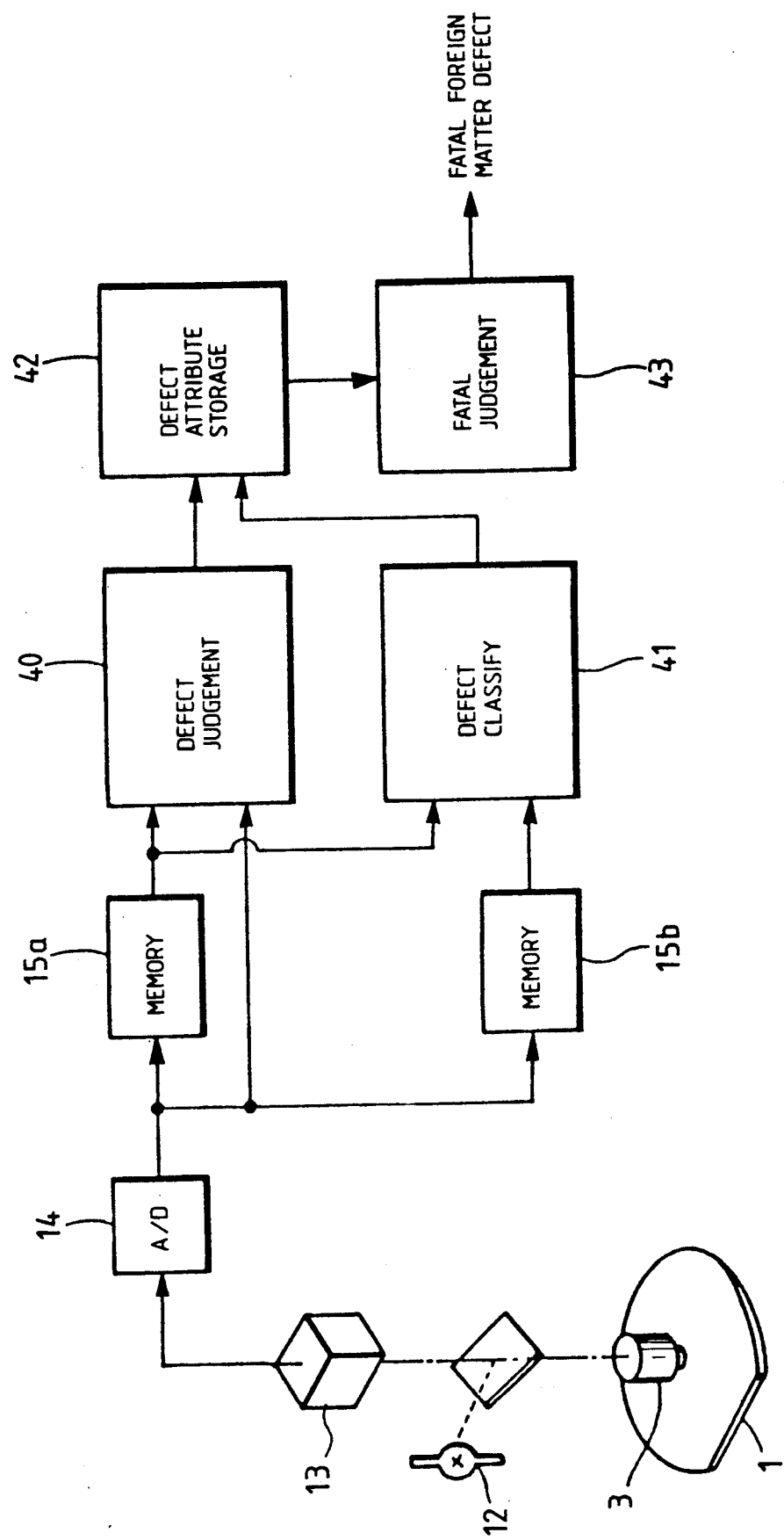
FIG. 22 shows an embodiment of a system for judging the fatalness of a foreign matter or contaminant defect utilizing a visual inspection device.
Figure 23:
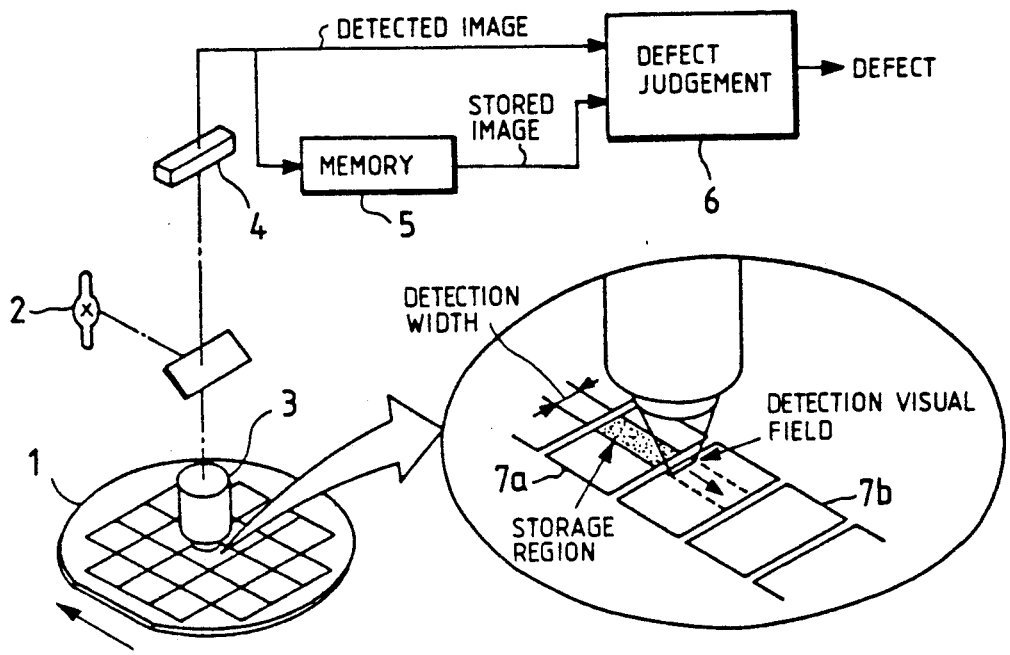
FIG. 23 shows a prior art defect detection device.
Figure 24:
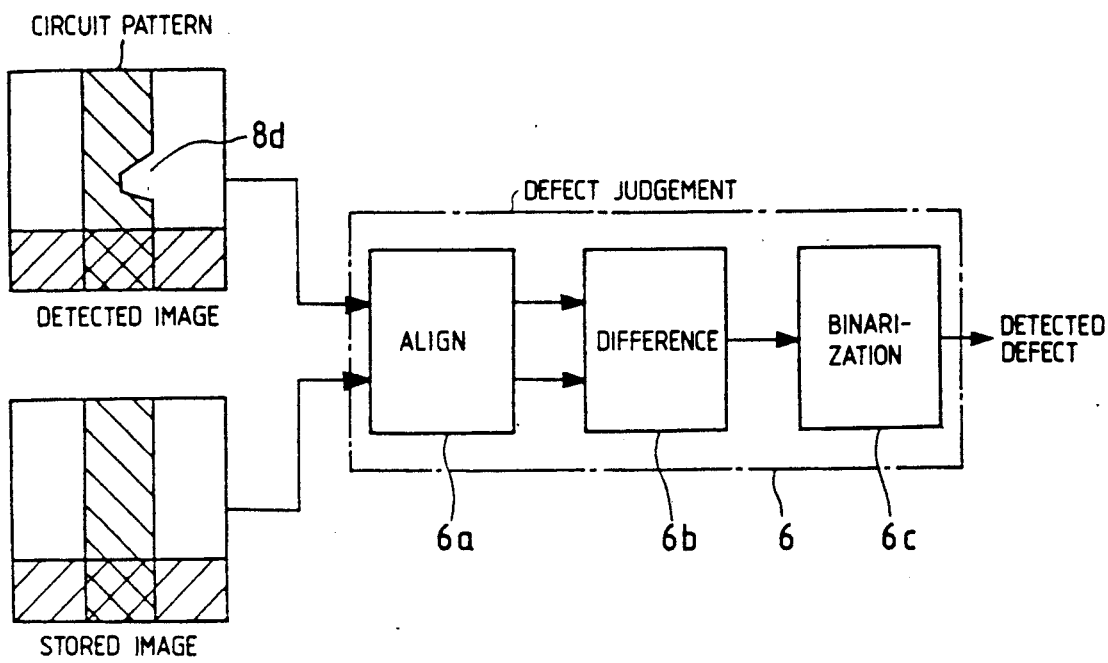
FIG. 24 shows a prior art defect detection device.

FIG. 22 shows a system for judging the fatalness of a foreign matter defect by using a visual inspection apparatus. In the figure, a defect is detected with a defect judgment section 40 and the coordinates are stored in a defect attribute storage section 42. For a detected defective portion, the defects are classified into foreign matter defects and other defects with the defect classification section 41 and are stored in the defect attribute storage section 42 coupled with their coordinates. After the same wafer is processed in the next process or device the wafer is inspected and defect judgment and classification are performed in a similar manner and the defect coordinates and the kind thereof are stored in the defect attribute storage section 42. For a defect which is judged to be a foreign matter defect in the preceding process or device its coordinates are examined at the fatalness judgment section 43 and if the defect is judged in the next process or device to be a deformation defect or a discoloration defect, the defect is judged to be a fatal defect.

Several embodiments have been described above, and in every case an object wafer images are detected and their positions are aligned to perform defect judgment and defect classification. At a place where the density of a circuit pattern on a wafer is small, it can occur that there is a pattern in the corner of one of the two images to be aligned and no pattern in the corresponding corner of the other image, which makes the accurate alignment of images impossible. Therefore, a dummy pattern is inserted into the area where no pattern is found so that in every detected image a pattern may be found and accurate alignment may be possible. A pattern of any shape can be used.

In the above embodiments, wafers have been referred to for explanatory purposes but the present invention can be utilized for semiconductor products such as TFT's or thin film magnetic heads.

According to the present invention, the defects detected with the visual inspection system can be automatically classified and visual observation is not needed. Foreign matter defects can be judged whether they are fatal or not. Thus the present invention can greatly contribute much to the development of the yield management of manufacturing process and facilities.

While we have shown and described several embodiments in accordance with the present invention, it is understood that the same is not limited thereto but is susceptible to numerous changes and modifications as known to one of ordinary skill in the art, and we therefore do not wish to be limited to the details shown and described herein but intend to cover all such modifications as are encompassed by the scope of the appended claims.

What is claimed is:

1. A defect detection method for a circuit pattern to be inspected comprising the steps of:
   obtaining multiple-focus image signals of the circuit pattern to be inspected by imaging with at least an image pickup means at different focal positions of the circuit pattern;
   aligning at least one image signal of the multiple-focus image signals of the circuit pattern to be inspected with at least a corresponding one image signal of multiple-focus image signals of a reference circuit pattern; and detecting a foreign matter defect on the circuit pattern so as to discriminate from a discoloration defect and a deformation defect on the circuit pattern in accordance with a density value of a difference image signal obtained by comparing at least the aligned one image signal of the multiple-focus image signals of the circuit pattern and the reference circuit pattern.

2. A defect detection method according to claim 1, wherein the step of obtaining multiple-focus images of the pattern to be inspected includes one of simultaneously obtaining a plurality of images of the pattern to be inspected at different focal positions and sequentially obtaining a plurality of images of the pattern to be inspected at different focal positions.

3. A defect detection method according to claim 1, wherein the corresponding reference circuit pattern has no defect and the multiple-focus image signals thereof are obtained by imaging with at least an image pickup means.

4. A defect detection method according to claim 1, further comprising the step of detecting the difference image signal obtained by comparing dark field image signals for the circuit pattern to be inspected and a corresponding reference circuit pattern having no defect.

5. A defect detection method according to claim 1, wherein the circuit pattern is an LSI wafer pattern.

6. A defect detection method according to claim 3, further comprising the step of detecting the discoloration defect in accordance with a density value of a difference image signal obtained by comparing differentiated image signals obtained by differential processing each of the aligned one image signals of the circuit pattern and the reference circuit pattern with each other.

7. A defect detection method according to claim 6, wherein a defect which is not determined to be one of a foreign matter defect and a discoloration defect is determined to be a deformation defect.

8. A defect detection method for a circuit pattern to be inspected which a circuit pattern is processed in a plurality of stages in respective processing devices, comprising the steps of:

performing inspection on the circuit pattern to be inspected before and after processing of the circuit pattern in a respective processing device by inspecting for at least two of a foreign matter defect, a discoloration defect and a deformation defect;

determining whether a defect occurs in a same position on the circuit pattern to be inspected before and after processing in the processing device; and classifying the defect as a fatal defect of the circuit pattern to be inspected, by detecting that the defect inspected as the foreign matter defect before processing in the processing device is detected upon inspection to be one of the discoloration defect and the deformation defect after processing in the processing device.

9. A defect detection method for a circuit pattern to be inspected according to claim 8, wherein the performing step comprises:

obtaining multiple-focus image signals of the circuit pattern to be inspected by imaging with at least an image pickup means at different focal positions of the circuit pattern, before and after processing of the circuit pattern in a respective processing device;

aligning at least one image signal of the multiple-focus image signals of the circuit pattern to be inspected with at least a corresponding one image signal of multiple-focus image signals of a reference circuit pattern before and after processing of the circuit pattern in a respective processing device; and detecting the foreign matter defect of the circuit pattern so as to discriminate from the discoloration defect and the deformation defect on the circuit pattern in accordance with a density value of a difference image signal obtained by comparing at least the one aligned image signal of the multiple-focus image signals of the circuit pattern and the reference circuit pattern before and after processing of the circuit pattern in a respective processing device.

10. A defect detection method according to claim 9, further comprising the step of discriminating the discoloration defect from the fatal defect in accordance with a density value of a difference image signal obtained by comparing differentiated image signals with each other obtained by differential processing each of the aligned one image signal of the circuit pattern and the reference circuit pattern.

11. A defect detection method according to claim 9, further comprising the step of detecting the discoloration defect in accordance with a density value of a difference image signal obtained by comparing dark field image signals for the circuit pattern to be inspected and a corresponding reference circuit pattern having no defect.

12. A defect detection system for a circuit pattern to be inspected comprising:

means for obtaining multiple-focus image signals of the circuit pattern to be inspected by imaging with at least an image pickup means at different focal positions of the circuit pattern;

means for aligning at least one image signal of the multiple-focus image signals of the circuit pattern to be inspected with at least a corresponding one image signal of multiple-focus image signals of a reference circuit pattern; and means for detecting a foreign matter defect of the circuit pattern so as to discriminate from a discoloration defect and a deformation defect on the circuit pattern in accordance with a density value of a difference image signal obtained by comparing with a comparing means at least the aligned one image signal of the multiple-focus image signals of the circuit pattern and the reference circuit pattern.

13. A defect detection system according to claim 12, wherein the means for obtaining multiple-focus images of the pattern to be inspected include means for one of simultaneously obtaining a plurality of images of the pattern to be inspected at different focal positions, and means for sequentially obtaining a plurality of images of the pattern to be inspected at different focal positions.

14. A defect detection system according to claim 12, wherein the means for simultaneously obtaining the plurality of images at different focal positions includes a plurality of image pickup means having different focal positions for simultaneously picking up an image of the pattern to be inspected.

15. A defect detection system according to claim 12, wherein the means for sequentially obtaining a plurality of images of the pattern to be inspected at different focal positions includes pickup means and means for moving the pattern to be inspected so as to place the pattern at different focal positions with respect to the pickup means, the pickup means obtaining an image of the pattern to be inspected at a plurality of different focal positions after movement of the pattern to the different focal positions by the moving means.

16. A defect detection system according to claim 12, further comprising memory means for storing multiple-focus image signals of the corresponding reference circuit pattern obtained by imaging with at least the image pickup means.

17. A defect detection system according to claim 12, further comprising means for detecting the discoloration defect in accordance with a density value of a difference image signal obtained by comparing dark field image signals for the circuit pattern to be inspected and a corresponding reference circuit pattern having no defect.

18. A defect detection system according to claim 12, further comprising memory means for storing multiple-focus image signals of the circuit pattern obtained by imaging with at least the image pickup means.

19. A defect detection system according to claim 12, further comprising means for detecting a defect by comparing an aligned one image signal of the circuit pattern and the reference circuit pattern so as to operate the multiple-focus image signals obtaining means when the defect is detected by the defect detecting means.

20. A defect detection system according to claim 19, wherein the means for detecting a defect includes discoloration defect determination means for determining a defect to be a discoloration defect comprising, differentiation means for differentiating the multiple-focus image of the pattern to be inspected and the corresponding reference pattern, means for comparing the differentiated images to provide a difference image signal of the compared differentiated images, and means for determining a discoloration defect in accordance with the difference signal.

21. A defect detection system according to claim 12, wherein the means for detecting a defect further includes discoloration defect determination means for determining a defect to be a discoloration defect comprising differentiation mean for differentiating the multiple-focus images of the pattern to be inspected and the corresponding reference pattern, means for comparing the differentiated images to provide a difference image signal of the compared differentiated images, and means for determining a discoloration defect in accordance with the difference signal.

22. A defect detection system according to claim 21, further comprising deformation determination means for determining a defect to be a deformation defect when the defect is not determined to be one of a foreign matter defect and a discoloration defect.

23. A defect detection system according to claim 21, wherein the discoloration defect determining means includes means for judging a defect to be a discoloration defect in accordance with values of difference image signals of the multiple-focus images of the pattern to be inspected and the corresponding reference pattern.

24. A defect detection system according to claim 19, further comprising storage means for storing the position of the defect detected by the defect detecting means.

25. A defect detection system for a circuit pattern to be inspected which a circuit pattern is processed in a plurality of stages in respective processing devices, comprising:

means for performing inspection on the circuit pattern to be inspected before and after processing of the circuit pattern in a respective processing device by inspecting for at least two of a foreign matter defect, a discoloration defect and a deformation defect;

means for determining whether a defect occurs in a same position on the circuit pattern to be inspected before and after processing in the processing device; and means for classifying the defect as a fatal defect of the circuit pattern to be inspected by detecting that the defect inspected as the foreign matter defect before processing in the processing device is detected to be one of the discoloration defect and the deformation defect after processing in the processing device.

26. A defect detection system for a circuit pattern to be inspected according to claim 25, wherein the performing means comprises:

means for obtaining multiple-focus image signals of the circuit pattern to be inspected by imaging with at least an image pickup means at different focal positions of the circuit pattern, before and after processing of the circuit pattern in a respective processing device;

means for aligning at least one image signal of the multiple-focus image signals of the circuit pattern to be inspected with at least a corresponding one image signal of multiple-focus image signals of a reference circuit pattern before and after processing of the circuit pattern in a respective processing device; and means for detecting the foreign matter defect of the circuit pattern so as to discriminate from the discoloration defect and the deformation defect on the circuit pattern in accordance with a density value of a difference image signal obtained by comparing at least the aligned one image signal of the multiple-focus image signals of the circuit pattern and the reference circuit pattern before and after processing of the circuit pattern in a respective processing device.

27. A defect detection system form a circuit pattern to be inspected according to claim 26, further comprising means for discriminating a discoloration defect from the fatal defect in accordance with a density value of a difference image signal obtained by comparing differentiated image signals obtained by differential processing each of the aligned one image signal of the circuit pattern and the aligned one image signal of the reference circuit pattern with each other.

28. A defect detection system for a circuit pattern to be inspected according to claim 27, further comprising means for detecting the discoloration defect in accordance with a density value of a difference image signal obtained comparing dark field image signals for the circuit pattern to be inspected and a corresponding reference circuit pattern having no defect.

* * * * *